United States Patent [19]

Siegel et al.

[11] Patent Number: 5,160,974
[45] Date of Patent: Nov. 3, 1992

[54] CLOSED SAMPLE CELL FOR USE IN FLOW CYTOMETRY

[75] Inventors: Jeffrey I. Siegel, Danbury, Conn.; Sidney Braginsky, Dixhills, N.Y.

[73] Assignee: Flow Science, Inc., Southport, Conn.

[21] Appl. No.: 542,967

[22] Filed: Jun. 25, 1990

[51] Int. Cl.⁵ .................................................. G01N 21/03
[52] U.S. Cl. ....................................... 356/246; 356/39
[58] Field of Search ........................................... 356/246, 39

[56] References Cited

U.S. PATENT DOCUMENTS

| | | | |
|---|---|---|---|
| 4,380,392 | 4/1983 | Karabegov et al. | 356/243 |
| 4,522,492 | 6/1985 | Bonner | 356/39 |
| 4,547,075 | 10/1985 | Fei | 356/39 |
| 4,675,019 | 6/1987 | Bellhouse et al. | 356/39 |

FOREIGN PATENT DOCUMENTS 644460 10/1950 United Kingdom ................ 356/246

Primary Examiner—Richard A. Rosenberger
Attorney, Agent, or Firm—Paul A. Fattibene; Arthur T. Fattibene

[57] ABSTRACT

A closed flow cell having a cavity with a flexible diaphragm at either end of a flow tube. A sample having particles or biological cells suspended in a fluid is placed within either cavity. Movement of the diaphragm forces the fluid to flow through the flow tube back and forth between the two cavities. Detectors are positioned adjacent the flow tube. A light source, typically a laser, illuminates the flow tube. Scattered light from the light source is detected by the detectors. Various properties of the particle are thereby determined.

3 Claims, 2 Drawing Sheets

CLOSED SAMPLE CELL FOR USE IN FLOW CYTOMETRY

FIELD OF INVENTION

This invention relates generally to cytometry and particularly to a closed cell for containing a sample to be analyzed by flow cytometry.

BACKGROUND OF THE INVENTION

Flow cytometry is a technique for analyzing properties of particles in suspension. Typically, cytometry is used to study properties of biological cells, cell clusters, or chromosomes. A cytometer is used to analyze a fluid sample having particles suspended therein. A sheath fluid is used to protect and contain the sample being analyzed. The sample fluid and the sheath fluid are directed past a series of detectors. Generally, these detectors measure only light intensities and cannot resolve details of the particles or biological cells being analyzed. Therefore, morphological details of a cell cannot be obtained. A light source, such as a laser, is used to illuminate the suspended particles as they flow past the detectors. Light scattered by the particles is measured. The light scatter provides an indication of particles or cell size and structure. In some applications, the particles or cells may have been treated to emit light as fluorescence, luminescence, or other type of illumination. The illumination is then detected. Cellular components or constituents can be measured with fluorescent stains or dyes for D.N.A., R.N.A., or specific proteins.

In order to control the fluid in which the suspended particles of interest are contained, relatively complex pumps and regulators are needed. A waste fluid collector is also needed to collect both the sheath fluid and the sample fluid. Typically, all of the waste fluids are combined into a single waste collector. Additionally, once a sample is analyzed, it flows into the waste fluid collector, preventing any possibility of subsequently identifying the sample. The waste fluid must also be disposed of. Since it is not possible to identify individual samples precautions must be taken with all of the waste consistent with the most harmful or dangerous sample that was analyzed.

Therefore, there is a need in flow cytometry to keep samples separate in order to facilitate the analysis of a sample multiple times if desired. Additionally, there is a need to contain a sample to prevent the spread of infectious diseases, which flow cytometry is often used to detect. There is also a need to separately store the samples after analysis should their identification and retrieval become necessary. Additionally, there is a need to provide safe disposal of analyzed samples once they are no longer needed.

SUMMARY OF THE INVENTION

The present invention comprises a closed sample cell for use in a flow cytometer. The closed sample cell has cavities at either end with a flow tube therebetween. A diaphragm is positioned at one end of each cavity. Detectors are positioned next to the flow tube to detect light reflected or emitted by the particles or cells suspended in a fluid as they pass through the flow tube. The diaphragms at either end of the closed cell can be moved back and forth to force the fluid containing the particles or biological cells to be analyzed from one end of the flow tube to the other. Detectors detect various properties of the suspended particles based upon scattered light, such as from a laser. A charge injector and transparent electrodes can be used to help align the suspended cells or particles as they pass through the flow tube. A cavitator can be used to break up cell or particle clusters prior to entering the flow tube. In one embodiment, the detectors are positioned adjacent the cell, and do not form a part thereof.

Accordingly, it is an object of the present invention to prevent the possibility of contamination to either the sample being analyzed or individuals handling the samples.

It is a further object of the present invention to provide convenient storage of samples for later identification, use, or analysis.

It is an advantage of the present invention that it permits a sample to flow past a detector multiple times.

It is yet another advantage of the present invention that it does not require laminar flow.

It is a further advantage of the present invention that it does not have to be purged or flushed after each sample is analyzed.

It is a feature of the present invention that it is a hermetically sealed closed cell.

It is another feature of the present invention that a two dimensional array is used to measure other particle parameters such as velocity or size.

It is yet another feature of the present invention that it is disposable.

These and other objects, advantages, and features will become readily apparent in view of the following more detailed description.

DETAILED DESCRIPTION OF THE PREFERRED EMBODIMENTS

Figure 1:
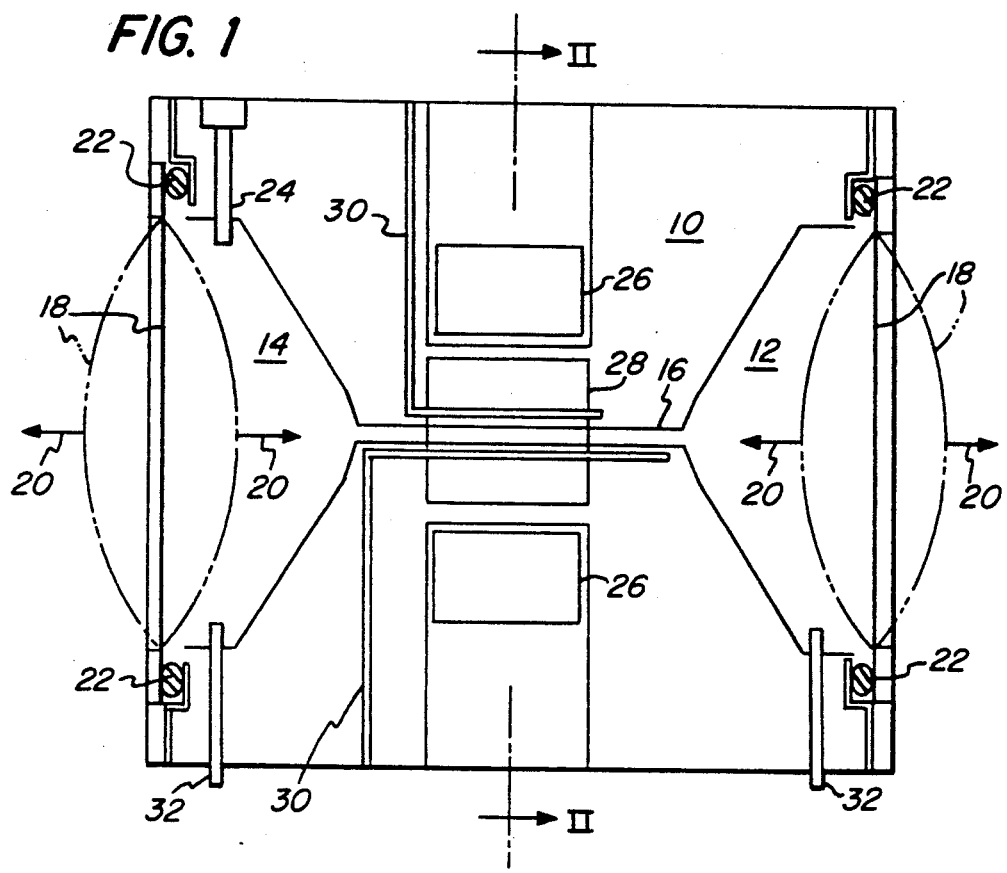
FIG. 1 is a top view generally illustrating the present invention.

FIG. 1 generally illustrates the present invention. A body 10 has two cavities therein; a first cavity 14 and a second cavity 12. The two cavities 12 and 14 can be of many different shapes, as long as the cavities 12 and 14 function to hold the sample being analyzed. The preferred shape is conical as ilustrated. The cavities 12 and 14 are connected by a flow tube 16. Diaphragms 18 are placed at either end of body 10 sealing the cavities 12 and 14. Each diaphragm 18 is secured to the body 10 by a seal 22. The diaphragms 18 hermetically seal the cavities 12 and 14. The diaphragms 18 can be made of any flexible material, such as rubber or synthetic material. Arrows 20 indicate the direction of motion of the diaphragms 18. Extending through body 10 and into cavity 14 is an injection port 24. Injection port 24 is adapted to receive a syringe needle for the injection of a sample to be analyzed.

Diode detectors 26 are mounted on two sides adjacent to the flow tube 16. Between the two diode detectors 26 and beneath the flow tube 16 is positioned a two dimensional solid state array detector 28. Closely adjacent the flow tube 16 are positioned transparent electrodes 30. A combination charge injector and cavitator 32 extends through the body 10 and into each cavity 12 and 14.

Figure 2:
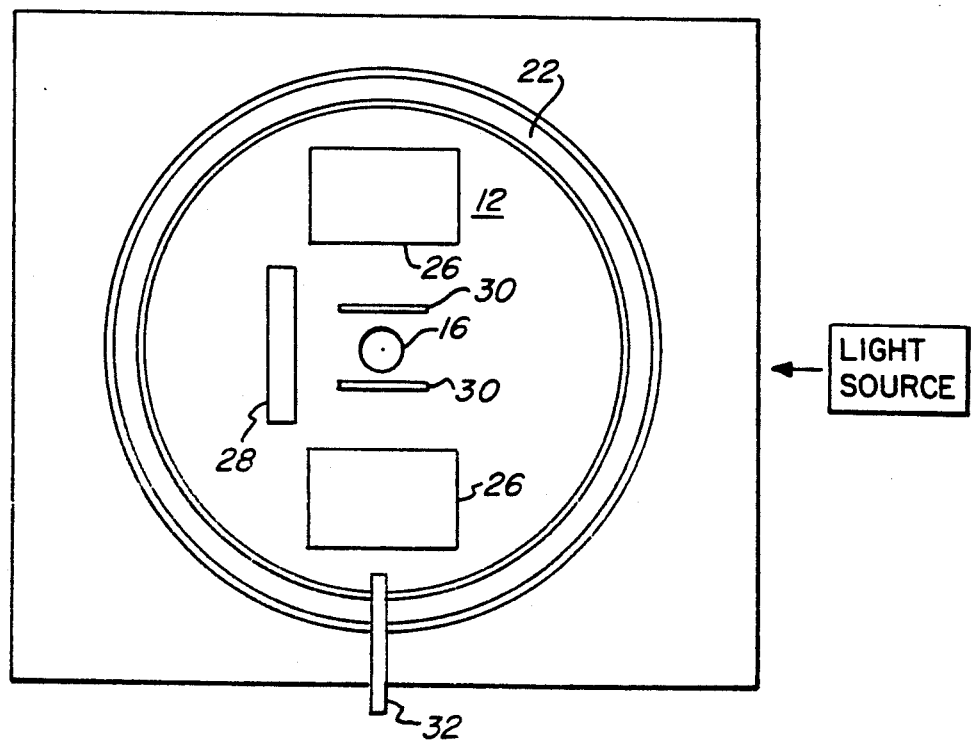
FIG. 2 is a cross section of FIG. 1 taken along line II—II.

The operation of the device can readily be appreciated with reference to FIGS. 1 and 2.

The device is intended to be place in a cytometer. Many of the conventional electrical and mechanical connections use in a conventional cytometer can be used. The sample in the present invention, however, is contained in the flow tube 16 during analysis. This is in contrast to the free flowing sample contained by a sheath fluid in the conventional cytometer.

Initially, the interior of the closed flow cell is evacuated. Therefore, when a syringe needle containing a sample to be analyzed is injected into the injection port 24, sufficient sample fluid is pulled into the sealed flow cell for analysis. Injection port 24 is made in a well known fashion so as to be self-sealing upon removal of the sample syringe needle. Once the sample is injected into a first cavity 14, the diaphragm 18 can be moved in the direction of arrows 20 to move the sample being analyzed through flow tube 16 and into second cavity 12. The sample to be analyzed can then be made to move back and forth between cavities 12 and 14 through flow tube 16 as desired. The motion of the diaphragms 18 can be easily automated by an electrical motor, which is not shown. The diameter of flow tube 16 can vary, depending on the particles or biological cells to be analyzed. Typically, the range of diameters will be from 10 to 400 microns.

As is best seen in FIG. 2, when a sample is to be analyzed, light source 34, which typically is a laser, is directed at flow tube 16. The diode detectors 26 are mounted sufficiently close to flow tube 16 so as to detect and measure any fluorescence, as well as forward and side scattered light reflected from the particle or biological cells being analyzed in the sample. In some applications a portion of the particle or cell being analyzed is marked with a fluorescent, luminescent, or other light emitting material. Generally, the marker adheres to a portion of a particle or cell depending on a predetermined characteristic of the particle or cell. The marker greatly facilitates identification of the predetermined characteristic of the particle or cell. Filters can be placed between the diode detectors 26 and the flow tube 16 in some applications to aid in the detection of the marker. Because the diode detectors 26 are positioned close to flow tube 16, non-integrated light collectors and imaging objects are not needed. The large depth of the field of the diode detectors 26, eliminates the need for laminar flow within tube 16. In some applications, light guides may be used for illumination and detection. Additionallly, photomultiplier detectors can be used if required by the spectral sensitivity or light intensity.

The two-dimensional solid state array detector 28 positioned between the two diode detectors 26 and below the flow tube 16 permits the measurement of speed, direction, particle size, particle numbers, and the identification of clumps. This provides additional information beneficial to sample analysis. A single or multi-dimensional array can also be used.

Various techniques can be used to help improve the particle flow through flow tube 16. A cavitator 32 is used in both cavities 12 and 14. The cavitator 32 can be a piezoelectric crystal that when excited, vibrates at a relatively high frequency. The effect of the cavitator 32 is to reduce the flow resistance and to separate the particles or cells which tend to clump together. A charge injector is additionally used. The charge injector is incorporated into the cavitator 32. The charge injector puts a coulomb charge on the particles or biological cells. This coulomb charge helps to prevent aggregation of particles or cells.

Figure 3:
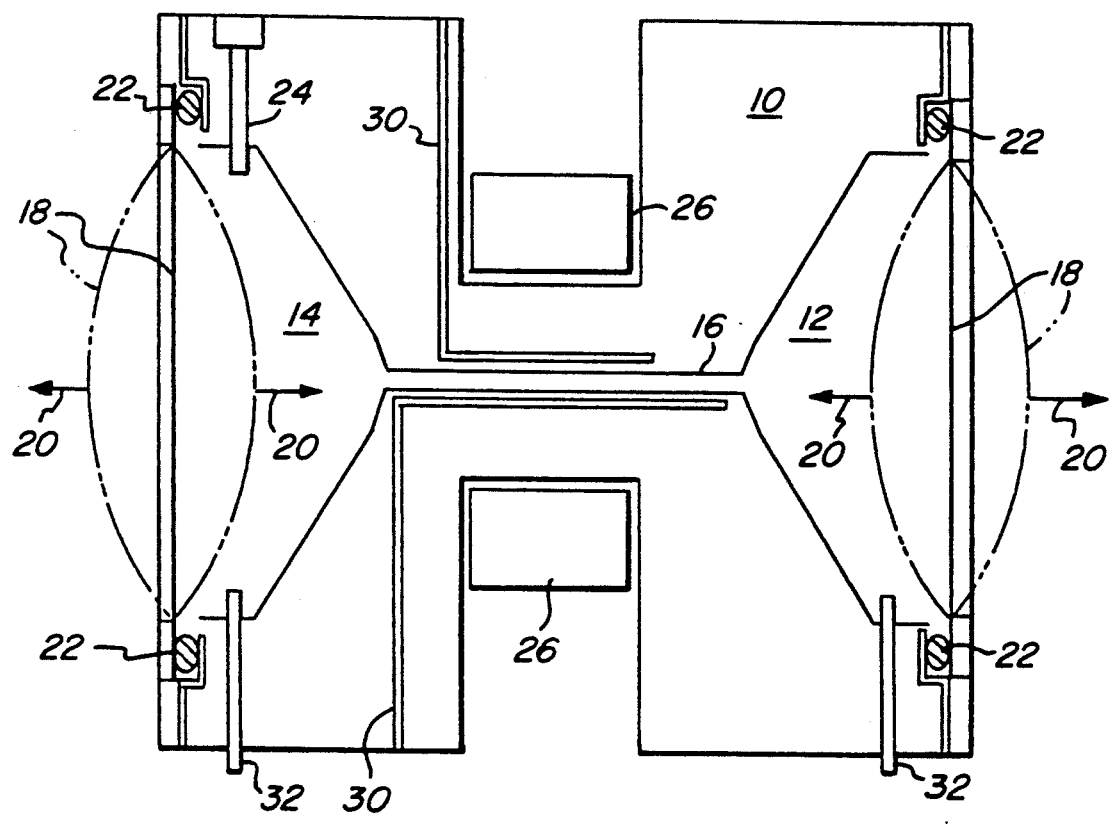
FIG. 3 is a top view generally illustrating another embodiment of the present invention.

FIG. 3 illustrates another embodiment of the present invention. In FIG. 3, the detectors 26 and 28 are not made part of the closed flow cell. The detectors 26 and 28 can be formed as a part of the flow cytometer apparatus, thereby reducing the cost of the closed flow cell. Therefore, the closed flow cell can be made more inexpensively facilitating its intended use, of one being used for each new sample to be analyzed.

Although the preferred embodiment has been illustrated and described, it will be obvious to those skilled in the art that various modifications may be made without departing from the spirit and scope of this invention.

What is claimed is:

1. A closed flow cell for use in flow cytometry comprising:
   a body;
   said body having a first cavity therein;
   said body having a second cavity therein;
   a flow tube connecting said first and second cavity;
   a first diaphragm sealing said first cavity;
   a second diaphragm sealing said second body;
   detector means, associated with said flow tube, for detecting predetermined properties of particles in suspension;
   a charge injector in said first and second cavity; and
   a transparent electrode positioned adjacent said flow tube, whereby movement of said first and second diaphragms causes a fluid to flow through said flow tube between said first and second cavities.

2. A closed flow cell for use in flow cytometry comprising:
   a body;
   said body having a first cavity therein;
   said body having a second cavity therein;
   a flow tube connecting said first and second cavity;
   a first diaphragm sealing said first cavity;
   a second diaphragm sealing said second body; and
   a cavitator in said first and second cavity,
   whereby movement of said first and second diaphragms causes a fluid to flow through said first tube between said first and second cavities.

3. A closed flow sample cell for use in flow cytometry comprising:
   a body, said body having a first end and a second end, said first end having a first cone shaped cavity therein, said second end having a second cone shaped cavity therein;
   a flow tube positioned between and connecting the smaller diameter ends of said first and second cone shaped cavities, said flow tube having a predetermined diameter based upon the particle size being analyzed;
   a first diaphragm sealing the larger exterior opening of said first cavity;
   a second diaphragm sealing the larger exterior opening of said second cavity;
   said body having an injection port extending from the exterior surface of said body into one of said first or second cavities;
   a self sealing membrane associated with said injection port;
   a pair of diode detectors positioned parallel to each other with said flow tube therebetween;

a pair of transparent electrodes positioned adjacent said flow tube between said flow tube and said pair of diode detectors;

a pair of cavitators, one positioned in each said first and second cavities; and a pair of charge injectors, one positioned in each said first and second cavities;

whereby predetermined properties of particles suspended in a fluid can be determined while remaining sealed within the cell.

* * * * *